(12) United States Patent
Nakakita et al.

(10) Patent No.: US 7,816,517 B2
(45) Date of Patent: Oct. 19, 2010

(54) SACCHARIDE FLUORESCENCE LABELING METHOD AND SACCHARIDE FLUORESCENCE LABELING APPARATUS

(75) Inventors: Shin-ichi Nakakita, Kagawa (JP); Sumihiro Hase, Suita (JP)

(73) Assignees: National University Coporation Kagawa University, Kagawa (JP); Osaka University, Osaka (JP)

( * ) Notice: Subject to any disclaimer, the term of this patent is extended or adjusted under 35 U.S.C. 154(b) by 266 days.

(21) Appl. No.: 11/885,847

(22) PCT Filed: Mar. 7, 2006

(86) PCT No.: PCT/JP2006/004406

§ 371 (c)(1),
(2), (4) Date: Feb. 19, 2008

(87) PCT Pub. No.: WO2006/095744

PCT Pub. Date: Sep. 14, 2006

(65) Prior Publication Data

US 2008/0177058 A1    Jul. 24, 2008

(30) Foreign Application Priority Data

Mar. 10, 2005    (JP) .............................. 2005-067793

(51) Int. Cl.
*C07H 1/00*    (2006.01)
(52) U.S. Cl. ..................................... 536/124
(58) Field of Classification Search ................... 536/124
See application file for complete search history.

(56) References Cited

U.S. PATENT DOCUMENTS 4,975,533 A * 12/1990 Kondo et al. ............... 536/55.3

OTHER PUBLICATIONS

A. Kondo et al. "Improved Method for Fluorescence Labeling of Sugar Chains with Sialic Acid Residues". Agricultural and Biological Chemistry, vol. 54, pp. 2169-2170. Aug. 1990.
S. Hase et al. "Tagging of Sugars with Fluorescent Compound, 2-Aminopyridine". The Journal of Biochemistry, vol. 85, No. 1 pp. 217-220. Jan. 1979.
A. K. Vrkic et al. "Using Non-Covalent Complexes to Direct the Fragmentation of Glycosidic Bonds in the Gas Phase". Jouranl of American Society for Mass Spectrometry, vol. 15, pp. 715-724. 2004.
Shin-ichi Nakakita et al. "Gas-Phase Pyridylamination of Saccharides: Development and Applications". Glycoconjugate Journal vol. 24, No. 6/7, p. 367. Oct. 2007.
Shin-ichi Nakakita et al. "Gas-Phase Pyridylamination of Saccharides: Development and Applications". Analytical Chemistry vol. 79., No. 7, pp. 2674-2679. Apr. 2007.
Shin-ichi Nakakita et al., "Gas-Phase Pyridylamination of Saccharides: Development and Applications". *Analytical Chemistry*, vol. 79, No. 7, pp. 2674-2679 (Apr. 1, 2007).
Shin-ichi Nakakita et al. "Gas-Phase Pyridylamination of Saccharides: Development and Applications". Analytical Chemistry vol. 24, No. 6/7, p. 367. Oct. 2007.

* cited by examiner

*Primary Examiner*—Shaojia Anna Jiang
*Assistant Examiner*—Ganapathy Krishnan
(74) *Attorney, Agent, or Firm*—Harness, Dickey & Pierce, P.L.C.

(57) ABSTRACT

In one embodiment of the present invention, a first test tube including therein a dehydrated sample containing a sugar chain and a labeling agent solution made of 2-aminopyridine/acetic acid are stored in a well-closed container with the first test tube and the labeling agent solution secluded from each other. The labeling agent solution is heated, and the 2-aminopyridine is evaporated so as to be in contact with the sugar chain, thereby obtaining a pyridylamination sugar chain from the sugar chain. As a result, it is possible to provide the saccharide fluorescence labeling apparatus and the saccharide fluorescence labeling method whereby it is possible to simplify and ensure an operation for reacting saccharide into the pyridylamination sugar chain.

5 Claims, 4 Drawing Sheets

(TIME)

SACCHARIDE FLUORESCENCE LABELING METHOD AND SACCHARIDE FLUORESCENCE LABELING APPARATUS

TECHNICAL FIELD

The present invention relates to a saccharide fluorescence labeling method and a saccharide fluorescence labeling apparatus each of which simplifies a fluorescence labeling operation using aminopyridine.

BACKGROUND ART

Structural analysis of a sugar chain of polysaccharide has such a problem that it is difficult to separate and purify a sugar chain. This is caused by the following condition: An amount of a complex sugar chain to be studied is extremely small, and the sugar chain has various types of structures, but sugar itself does not have any marker group.

Conventionally, there has been widely known a method in which a fluorescence labeling group is introduced into a reducing end of a sugar chain of a saccharide so as to confirm analysis or identification of the saccharide with high sensitivity and high accuracy. The inventors of the present invention has developed a pyridylamination method in which a fluorescence labeling group is introduced into the reducing end of the saccharide. As illustrated in FIG. 4, the method is such that 2-aminopyridine serving as the fluorescence labeling group is introduced into the reducing end of the sugar chain so as to obtain the fluorescence-labeled saccharide (pyridylaminated sugar chain).

The analysis of the sugar chain which is carried out by using the pyridylaminated sugar chain has the following advantages.
(1) High sensitivity (detection of 1 fmol amount is possible)
(2) High stability (a pyridylaminated sugar chain prepared 10 years ago has currently no change in fluorescence intensity)
(3) High resolution (a combination with high-performance liquid chromatography (HPLC) allows 1000 sugar chains to be separated)
(4) High versatility (highly compatible with mass spectrometry (MS))
(5) Quantification is possible (only one portion is allowed to enter a single sugar chain)

An example of the conventional pyridylamination method is as follows. First, 20 μl (micro litter: 1 μl corresponds to $10^{-9}$ $m^3$) of 2-aminopyridine/acetic acid (552 mg/200 μl) is added to a sample containing a sugar chain, and the resultant is sufficiently stirred, and then is heated at 90° C. for 60 minutes. After the reaction, 70 μl of borane-dimethylamine complex/acetic acid/water (200 mg/80 μl/50 μl) is added thereto, and the resultant is sufficiently stirred, and then is heated at 80° C. for 35 minutes. After the reaction, extraction is carried out by using an organic solvent and foreign matters are removed by using a cation exchange resin, thereby obtaining a pyridylaminated sugar chain.

Further, preparation of a sample containing a sugar chain is carried out by liberating a sugar chain from a glycoprotein or the like. Roughly, there are two methods for liberating a sugar chain. One is a method adopting chemical reaction. The other is a method adopting enzyme reaction.

Herein, hydrazinolysis is described as the method for liberating an N-linked sugar chain from a glycoprotein through chemical reaction. The hydrazinolysis is as follows. As illustrated in FIG. 5 for example, a sample (glycoprotein) is sufficiently dried by lyophilisation or the like and the resultant is mixed with hydrazine anhydride so as to completely dissolve the sample. The resultant is heated at 100° C. for 10 hours. Thereafter, the hydrazine anhydride is distilled under reduced pressure, and a portion having an acetyl group desorped by the hydrazinolysis is acetylated again by using saturated sodium hydrogen carbonate aqueous solution and acetic anhydride, thereby liberating a sugar chain from the glycoprotein.

DISCLOSURE OF INVENTION

Problems to be Solved by Invention

However, according to the conventional method, it may be difficult to dissolve the sample in 20 μl of 2-aminopyridine/acetate solution depending on an amount of impurities of the sample and a condensation process, so that it takes trouble to analyze saccharide, that is, the aforementioned analysis is carried out in an uncertain manner.

Further, according to the conventional method, if an organic solvent is used in removing an excess reagent after the reaction, monosaccharide to trisaccharide move to an organic layer and are separated from one another, so that it is necessary to carry out gel filtration in carrying out analysis of monosaccharide to the trisaccharide, so that it takes time and trouble to carry out the analysis.

Means to Solve the Problems

The present invention was made in order to solve the foregoing problems, and an object of the present invention is to realize a saccharide fluorescence labeling method and a saccharide fluorescence labeling apparatus whereby it is possible to simplify and ensure saccharide analysis.

In order to solve the foregoing problems, a saccharide fluorescence labeling method according to the present invention, in which a reducing end of a sugar chain is pyridylaminated so as to fluorescence-label the sugar chain, said method comprising the step of bringing 2-aminopyridine in a gasiform state into contact with the sugar chain.

The saccharide fluorescence labeling method may be arranged so as to comprise the steps of: storing a sample containing a sugar chain and a labeling agent solution containing 2-aminopyridine in a well-closed container so that the sample and the labeling agent solution are secluded from each other; and heating the labeling agent solution so as to evaporate the 2-aminopyridine so that the 2-aminopyridine having been evaporated comes into contact with the sugar chain.

It is preferable to arrange the saccharide fluorescence labeling method so that the 2-aminopyridine in a gasiform state is brought into contact with the sugar chain in an acidulous atmosphere. It is preferable to arrange the saccharide fluorescence labeling method so that acetic acid is used to form the acidulous atmosphere.

It is preferable to arrange the saccharide fluorescence labeling method so that the reducing end of the sugar chain and a reducer for reducing a —CH═N— group of a reaction intermediate with the 2-aminopyridine is brought into contact with the reaction intermediate while the reducer is in a gasiform state. It is preferable to arrange the saccharide fluorescence labeling method so that a borane-dimethylamine complex is used as the reducer.

In order to solve the foregoing problems, a saccharide fluorescence labeling apparatus according to the present invention comprising means which is capable of realizing the saccharide fluorescence labeling method based on any one of the aforementioned arrangements.

In order to solve the foregoing problems, another saccharide fluorescence labeling apparatus according to the present invention comprising: a container for storing therein a sample containing a sugar chain, a labeling agent solution containing 2-aminopyridine, a reducing end of the sugar chain, and a reducer for reducing a —CH=N— group of a reaction intermediate with the 2-aminopyridine; wall sections for inhibiting contact among the sample, the labeling agent solution, and the reducer, which are stored in a solution state; and openings respectively provided on the wall sections so as to bring the labeling agent solution and the reducer into contact with the sample while each of the labeling agent solution and the reducer is in a gasiform state.

Effects of Invention

As described above, the saccharide fluorescence labeling method according to the present invention, in which a reducing end of a sugar chain is pyridylaminated so as to fluorescence-label the sugar chain, includes the step of bringing 2-aminopyridine in a gasiform state into contact with the sugar chain.

According to the method, 2-aminopyridine in a gasiform state is brought into contact with the sample containing the sugar chain so as to pyridylaminate the reducing end of the sugar chain, so that it is not necessary to dissolve the sample containing the sugar chain unlike the conventional method and it is possible to avoid occurrence of an excess reagent after, reaction, thereby making it unnecessary to use an organic solvent for removing the excess reagent.

As a result, the aforementioned method makes it unnecessary to dissolve the sample and allows saccharide analysis to be simplified and ensured, and the method also makes it unnecessary to use an organic solvent for removing an excess reagent, thereby simplifying analysis of monosaccharide to trisaccharide.

As described above, the saccharide fluorescence labeling apparatus according to the present invention includes means being capable of realizing the aforementioned saccharide fluorescence labeling method.

According to the arrangement, the saccharide fluorescence labeling apparatus includes means capable of realizing the aforementioned saccharide fluorescence labeling method, so that it is unnecessary to dissolve the sample and it is possible to simplify and ensure saccharide analysis, and also it is unnecessary to use an organic solvent for removing an excess reagent, thereby simplifying analysis of monosaccharide to trisaccharide.

As described above, another saccharide fluorescence labeling apparatus according to the present invention includes: a container for storing therein a sample containing a sugar chain, a labeling agent solution containing 2-aminopyridine, a reducing end of the sugar chain, and a reducer for reducing a —CH=N— group of a reaction intermediate with the 2-aminopyridine; wall sections for inhibiting contact among the sample, the labeling agent solution, and the reducer, which are stored in a solution state; and openings respectively provided on the wall sections so as to bring the labeling agent solution and the reducer into contact with the sample while each of the labeling agent solution and the reducer is in a gasiform state.

According to the arrangement, the saccharide fluorescence labeling apparatus includes the wall sections and the openings, so that it is unnecessary to dissolve the sample and it is possible to simplify and ensure saccharide analysis, and also it is unnecessary to use an organic solvent for removing an excess reagent, thereby simplifying analysis of monosaccharide to trisaccharide.

For a fuller understanding of the nature and advantages of the invention, reference should be made to the ensuing detailed description taken in conjunction with the accompanying drawings.

REFERENCE NUMERALS

1 Container
1a Labeling agent solution
2 First test tube
2a Sample
3 Second test tube
3a Reducer
5 Heater

BEST MODE FOR CARRYING OUT THE INVENTION

With reference to FIG. 1 to FIG. 5, the following describes embodiments of a saccharide fluorescence labeling apparatus according to the present invention and a saccharide fluorescence labeling method according to the present invention.

Embodiment 1

Figure 1:
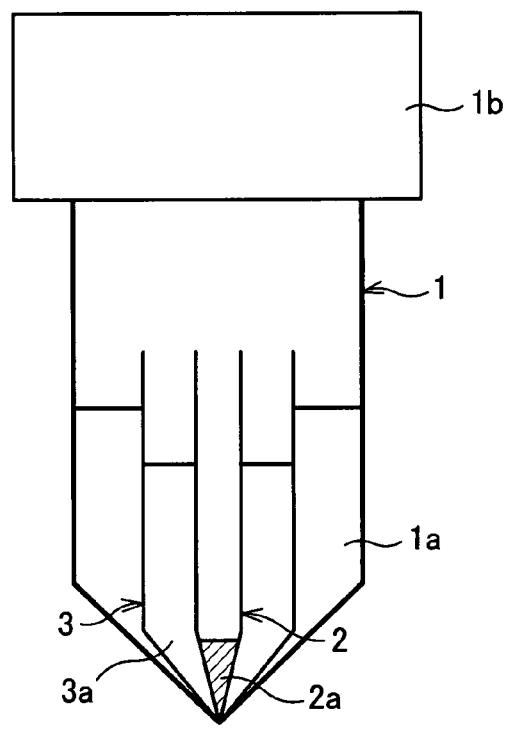
FIG. 1 is a front view illustrating Embodiment 1 of a saccharide fluorescence labeling apparatus for realizing a saccharide fluorescence labeling method according to the present invention.

As illustrated in FIG. 1, a saccharide fluorescence labeling apparatus of Embodiment 1 according to the present invention includes a bottomed-cylinder container (well-closed container) 1 having a volume of 30 ml for example and having a detachable screw cap 1b which allows an upper opening of the container 1 to be well closed. In the container 1, a shape of a portion extending from a cylindrically outer bottom to a cylindrically inner bottom is not particularly limited, but it is preferable that the shape is planate or gradually tapered toward its lower end. Particularly, it is preferable that the shape is tapered since the tapered shape allows the container 1 to be easily stored in a test tube rack.

In the container 1, a bottomed-cylindrical first test tube 2 and a bottomed-cylindrical second test tube 3 each of which has a diameter smaller than an internal diameter of the container 1 are provided so that they are preferably detachable from the container 1. An external diameter of each of the first and second test tubes 2 and 3 is set so as to be smaller than the internal diameter of the container 1, and an external diameter of the first test tube 2 is set so as to be smaller than an internal diameter of the second test tube 3. Thus, the second test tube 3 can be stored in the container 1, and the first test tube 2 can be stored in the second test tube 3.

Further, when the second test tube 3 is placed in the container 1 so that its bottom is in contact with the bottom of the container 1, it is preferable that the second test tube 3 can be fixed in the container 1 and kept upright therein. Thus, it may be so arranged that the shape of the outer bottom of the second test tube 3 is tapered so as to correspond to the tapered shape of the cylindrically inner bottom of the container 1. As a result, when the second test tube 3 is placed in the container 1 so that the bottom of the second test tube 3 is in contact with the bottom of the container 1, the second test tube 3 can be kept upright in the same axis as the container 1.

While, when the first test tube 2 is placed in the second test tube 3 so that the bottom of the first test tube 2 is in contact with the bottom of the second test tube 3, it is preferable that the first test tube 2 is fixed in the second test tube 3 and is kept upright therein. Thus, it may be so arranged that the shape of an outer bottom of the first test tube 2 is tapered so as to correspond to the tapered shape of the internal bottom of the second test tube 3. As a result, when the first test tube 2 is placed in the second test tube 3 so that the bottom of the first test tube 2 is in contact with the bottom of the second test tube 3, the first test tube 2 can be kept upright in the same axis as the second test tube 3.

Next, the following describes the saccharide fluorescence labeling method of Embodiment 1 according to the present invention in which the aforementioned fluorescence labeling apparatus is used. In the fluorescence labeling method, for example, 2 nmol of reducing sugar (e.g., glucosamine) is dissolved in 400 µl of 0.1% (V/V) acetic acid in the first test tube 2 and is dried (preferably subjected to lyophilisation), and the dried resultant is used as a sample 2a.

While, 400 µl of 2-aminopyridine/acetic acid (1 g/400 µl) is separately prepared as a labeling agent solution 1a, and the labeling agent solution 1a is poured into the container 1. Further, 400 µl of borane-dimethylamine complex/acetic acid/water (800 mg/320 µl/200 µl) is separately prepared as a reducer 3a, and the reducer 3a is poured into the second test tube 3.

Subsequently, the second test tube 3 is stored in the container 1, and the first test tube 2 is stored in the second test tube 3. Note that, it may be so arranged that: the second test tube 3 is stored in the container 1 beforehand, and the labeling agent solution 1a and the reducer 3a are poured into the container 1 and the second test tube 3 respectively, and the first test tube 2 having the sample 2a therein is stored in the second test tube 3. As a result, the sample 2a is secluded from the labeling agent solution 1a and the reducer 3a, and the labeling agent solution 1a is secluded from the reducer 3a in a liquid state.

Thereafter, the container 1 in which the first test tube 2 and the second test tube 3 have been stored are well closed by the screw cap 1b, and then the container 1 is heated at 100° C. for 120 minutes with it left still, and the labeling agent solution 1a and the reducer 3a in a vapor (gas) state are brought into contact with the sample 2a via a top opening shared by the container 1 and the second test tube 3, a top opening shared by the second test tube 3 and the first test tube 2, and a top opening of the second test tube 2, thereby promoting pyridylamination reaction.

After the reaction, the first test tube 2 having the reacted sample therein is retrieved from the container 1. In the reacted sample, a peak (black arrow) of a pyridylamination sugar chain is confirmed by size fractionation HPLC illustrated in FIG. 2. This shows that the pyridylamination sugar chain is generated.

In the aforementioned method, it is substantially unnecessary to remove reagent such as 2-aminopyridine/acetic acid and borane-dimethylamine complex/acetic acid/water after the reaction, and it is possible to simplify the aforementioned removal, and it is possible to simplify analysis carried out with respect to monosaccharide which has been conventionally difficult to analyze. Also, according to the present invention, it is possible to contribute to methylation analysis with high sensitivity and the analysis can be carried out in a single-pot reaction, so that it is possible to simplify the reaction operation.

Figure 2:
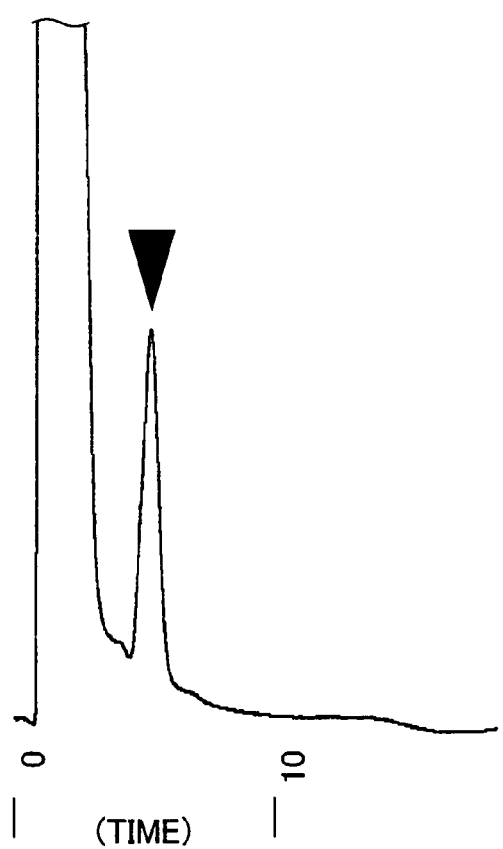
FIG. 2 is a chromatograph indicative of a state in which a pyridylamination sugar chain is generated by the fluorescence labeling method.

Note that, the reducer 3a includes water, but the peak of the pyridylamination sugar chain illustrated in FIG. 2 is confirmed. This shows that the presence of water does not have any influence on the reaction carried out in the present method. Water in the aforementioned reaction is mixed with the reducer so as to reduce an internal condition of the container 1, and the condition is different from a condition under which water exists in the reaction solution. This may have no influence on promotion of the reaction.

Embodiment 2

Figure 3:
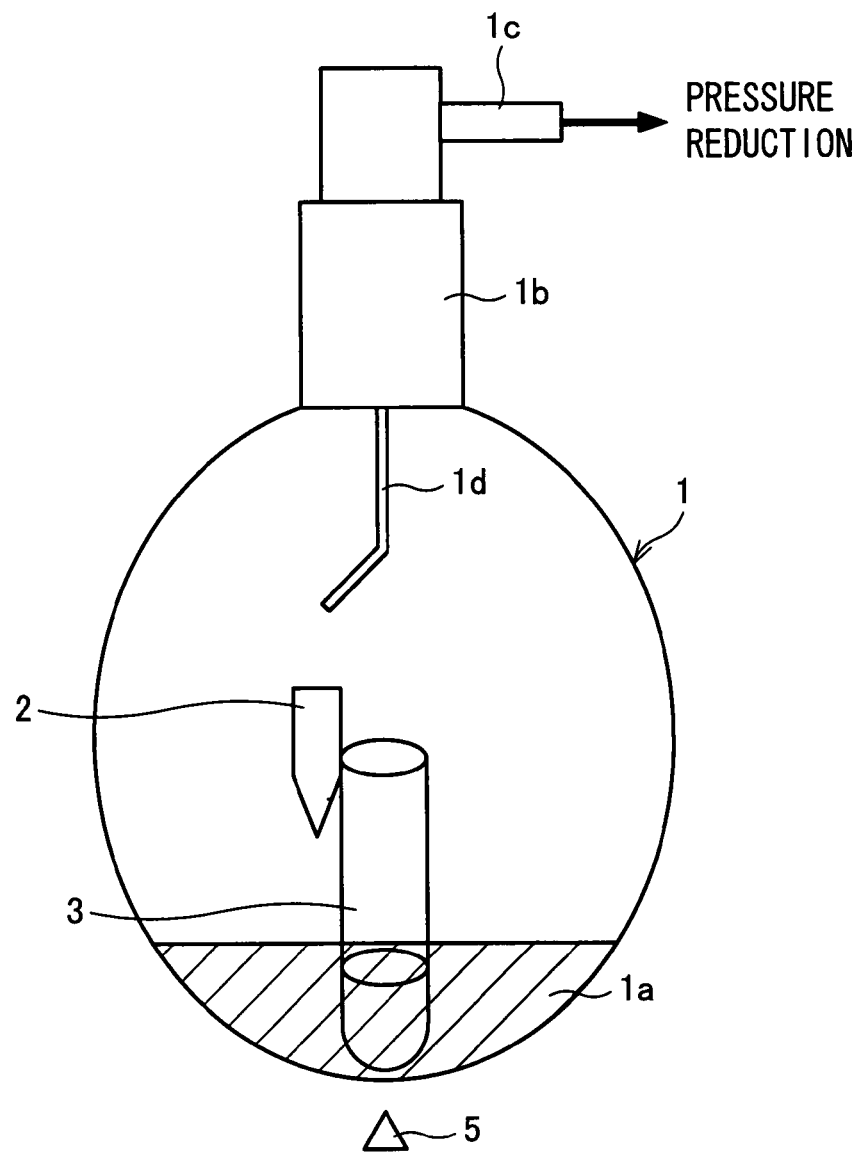
FIG. 3 is a front view illustrating Embodiment 2 of a saccharide fluorescence labeling apparatus according to the present invention.
Figure 4:
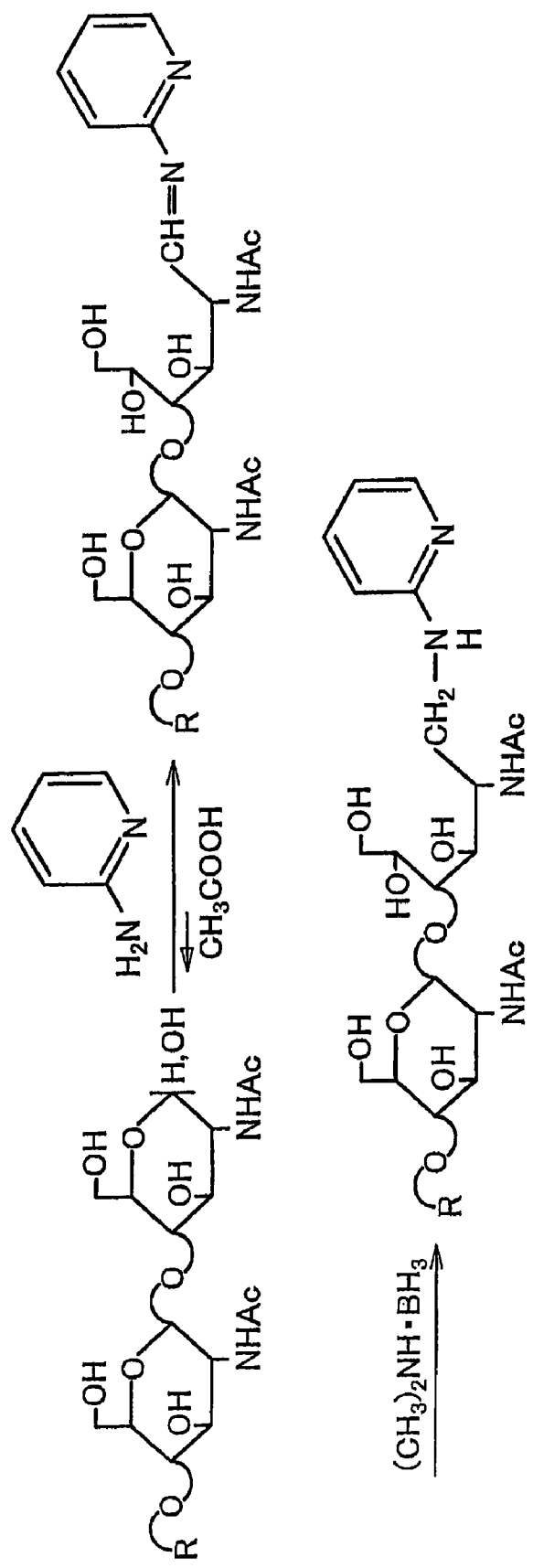
FIG. 4 illustrates a chemical formula indicative of each step of reacting saccharide into a pyridylaminated sugar chain.
Figure 5:
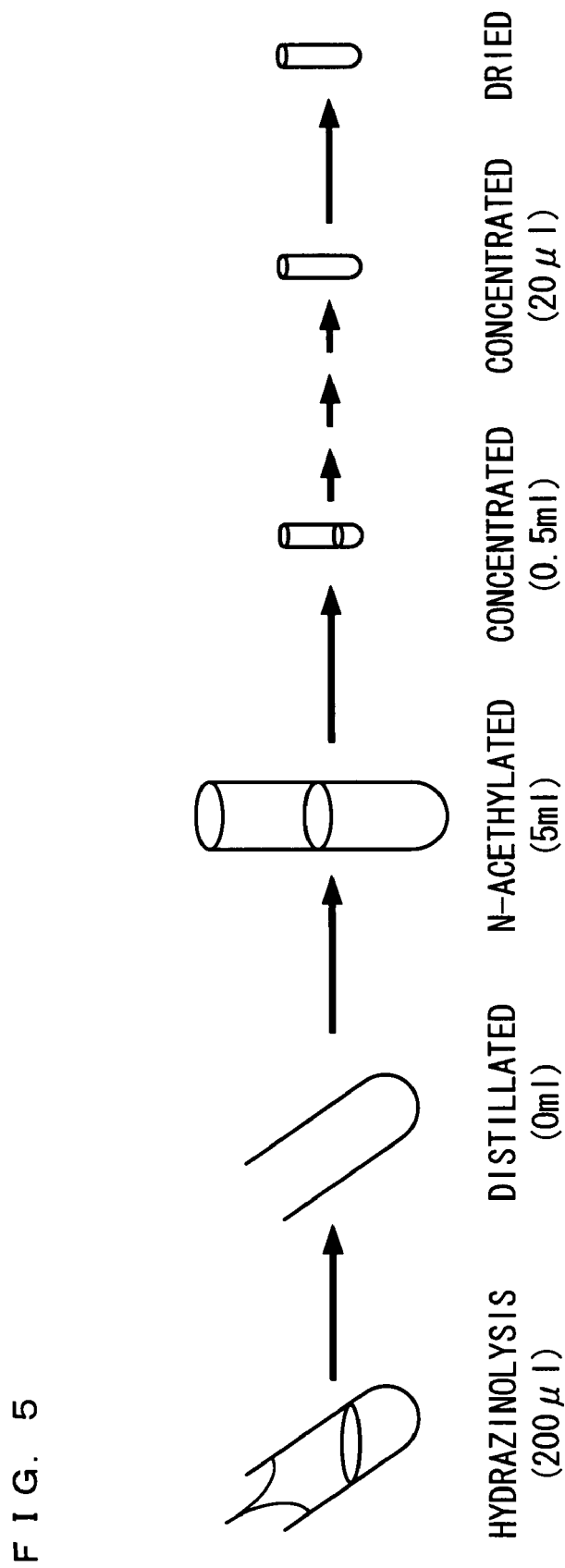
FIG. 5 is a front view indicative of pre-treatment steps of reacting saccharide into a pyridylaminated sugar chain.

A saccharide fluorescence labeling apparatus of Embodiment 2 according to the present invention is arranged as follows: As illustrated in FIG. 3, an eggplant-shaped flask (well-closed) container 1 made of glass has: a screw cap 1b which allows the container 1 to be well closed; a pressure adjustment conduit 1c for adjusting (reducing for example) an internal pressure of the container 1; and a gas conduit 1d for adjusting an internal pressure of the container 1. The pressure adjustment conduit 1c is provided on a top of the screw cap 1b.

The gas conduit 1d extends from a center of a bottom of the screw cap 1b along a rotational axis of the screw cap 1b, and an end of the gas conduit 1d is bent toward an opening of a first test tube 2 serving as a sample vial described later.

Further, the container 1 has therein the first test tube 2 and a second test tube 3 serving as a reducer test tube in which borane-dimethylamine complex/acetic acid/water is poured as reducer. The second test tube 3 is made of ceramics or metal so as to have a bottom and has an opening in its end in a longer side direction. Further, the second test tube 3 is provided in the container 1 so that its opening faces the screw cap 1b, and the second test tube 3 is detachably provided upright so that its longer side direction is along the rotational axis of the screw cap 1b.

The first test tube 2 is made of glass or metal so as to have a bottom, and has a vial opening in its end in a longer side direction, and has a tapered portion whose diameter is gradually reduced toward its other end in the longer side direction. Thus, the first test tube 2 allows a sample to adhere to its inside wall as a thin dried-and-solidified layer through a centrifugal operation or the like.

Further, the first test tube 2 can be detachably provided on an external periphery of the opening of the second test tube 3. Thus, an inverted-L-shaped hook section (not shown) is provided on a substantially central portion of an external peripheral face of the first test tube 2. As a result, when the first test tube 2 is provided on the opening of the second test tube 3, the vial opening of the first test tube 2 is positioned upper than the opening of the second test tube 3.

The first test tube 2 and the second test tube 3 are provided in the container 1, so that the sample contained in the first test tube 2, the reducer 3a contained in the second test tube 3, and the labeling agent solution 1a can be secluded from one another even though the aforementioned labeling agent solution 1a is poured into the container 1. Further, in the fluorescence labeling apparatus, a heater 5 for heating the container 1 upwardly is provided.

In the fluorescence labeling apparatus, the second test tube 3 having therein the reducer 3a is set in a bath of the labeling agent solution 1a contained in the container so that the opening of the second test tube 3 is positioned above a solution surface of the bath, and the first test tube 2 having in its inside wall a thin sample layer is set so that the vial opening of the first test tube 2 is positioned above the solution surface of the bath, thereby separating the sample, the reducer 3a, and the labeling agent solution 1a from one another.

If the container 1 is heated upwardly by the heater 5 under this condition, vapor of 2-aminopyridine and acetic acid is emitted from the labeling agent solution 1a and comes into contact with the sample in the first test tube 2 as a gas so as to react therewith, and the reducer 3a in the second test tube 3 subsequently evaporates and reacts as a gas in the first test tube 2, and then a reducing end of a sugar chain in the sample is pyridylaminated, thereby fluorescence-labeling the sugar chain.

Thereafter, the heating operation of the heater 5 is stopped, and the internal pressure of the container 1 is reduced (absorbed) via the pressure adjustment conduit 1c and the gas conduit 1d, so that it is possible to rapidly remove an excess vapor of 2-aminopyridine, acetic acid, and reducer 3a in the first test tube 2.

As described above, according to the saccharide fluorescence labeling apparatus of the present invention and the saccharide fluorescence labeling method of the present invention, unlike the conventional art, it is not necessary to dissolve a sample in 2-aminopyridine/acetic acid, and the sample is reacted with gaseous 2-aminopyridine under a reduction condition, so that an amount of an excess reagent remaining in the first test tube 2 serving as a reaction vial is small, and a step of removing the excess reagent by using an organic solvent can be omitted, so that also monosaccharide to trisaccharide can be favorably analyzed, thereby simplifying and ensuring an operation for reacting saccharide into a pyridylamination sugar chain.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The saccharide fluorescence labeling apparatus according to the present invention and the saccharide fluorescence labeling method according to the present invention can simplify and ensure an operation for reacting saccharide into a pyridylamination sugar chain, so that the saccharide fluorescence labeling apparatus and the saccharide fluorescence labeling method are favorably applicable to biochemistry and food fields in which it is necessary to analyze polysaccharide and saccharide.

The invention claimed is:

1. A saccharide fluorescence labeling method, in which a reducing end of a sugar chain is pyridylaminated so as to fluorescence-label the sugar chain,
    said method comprising the step of bringing 2-aminopyridine in a gasiform state into contact with the sugar chain.

2. The method as set forth in claim 1, comprising the steps of:
    storing a sample containing a sugar chain and a labeling agent solution containing 2-aminopyridine in a well-closed container so that the sample and the labeling agent solution are secluded from each other; and
    heating the labeling agent solution so as to evaporate the 2-aminopyridine so that the 2-aminopyridine having been evaporated comes into contact with the sugar chain.

3. The method as set forth in claim 1, wherein the 2-aminopyridine in a gasiform state is brought into contact with the sugar chain in an acidulous atmosphere.

4. The method as set forth in claim 3, wherein acetic acid is used to form the acidulous atmosphere.

5. The method as set forth in claim 1, wherein a —CH=N- group of a reaction intermediate between the reducing end of the sugar chain and the 2-aminopyridine is reduced to a secondary amine by bringing a borane-dimethylamine complex into contact with the reaction intermediate while the borane-dimethylamine complex is in a gasiform state.

* * * * *

UNITED STATES PATENT AND TRADEMARK OFFICE
CERTIFICATE OF CORRECTION

PATENT NO. : 7,816,517 B2
APPLICATION NO. : 11/885847
DATED : October 19, 2010
INVENTOR(S) : Shin-ichi Nakakita and Sumihiro Hase It is certified that error appears in the above-identified patent and that said Letters Patent is hereby corrected as shown below:

Title Page; should read;

(86)    PCT No.:    PCT/JP2006/304406

Signed and Sealed this
Twenty-fourth Day of May, 2011

David J. Kappos
*Director of the United States Patent and Trademark Office*